United States Patent
Takeda et al.

(10) Patent No.: US 7,993,631 B2
(45) Date of Patent: Aug. 9, 2011

(54) OIL BASE AND EXTERNAL PREPARATION CONTAINING SAME

(75) Inventors: Kyoichi Takeda, Chiba (JP); Yuki Kokeguchi, Chiba (JP); Hidetoshi Sone, Chiba (JP); Kiyotaka Kawai, Chiba (JP)

(73) Assignee: Kokyu Alcohol Kogyo Co., Ltd., Chiba (JP)

( * ) Notice: Subject to any disclaimer, the term of this patent is extended or adjusted under 35 U.S.C. 154(b) by 648 days.

(21) Appl. No.: 11/786,698

(22) Filed: Apr. 12, 2007

(65) Prior Publication Data

US 2007/0269470 A1    Nov. 22, 2007

Related U.S. Application Data

(60) Provisional application No. 60/792,286, filed on Apr. 14, 2006.

(51) Int. Cl.
*A61K 8/02* (2006.01)
*A61K 47/14* (2006.01)

(52) U.S. Cl. ........... 424/64; 424/401; 514/785; 554/124

(58) Field of Classification Search .................. 424/401; 514/785; 554/124
See application file for complete search history.

(56) References Cited

U.S. PATENT DOCUMENTS

2006/0204460 A1 *  9/2006  Takeda et al. .................. 424/64

FOREIGN PATENT DOCUMENTS

| JP | 11-128713 | 5/1999 |
| JP | 2003-238332 | 8/2003 |
| JP | 2004-256515 | 9/2004 |
| JP | 2004-256539 | 9/2004 |
| JP | 2005-036005 | 2/2005 |
| JP | 2005-132729 | 5/2005 |
| JP | 2005-179377 | 7/2005 |

OTHER PUBLICATIONS

Nishida, M. et al., "Emulsion stabilizer", May 18, 1999, JP 11-128713, machine translation.*
Takeda, K. et al., "Cosmetic", Jul. 7, 2005, JP 2005-179377, machine translation.*

* cited by examiner

*Primary Examiner* — Gina C Yu
(74) *Attorney, Agent, or Firm* — Wolf, Greenfield & Sacks, P.C.

(57) ABSTRACT

To provide an oil base having appropriate hardness and viscosity and excellent spreadability, a process for producing same, and a cosmetic material containing the oil base
The oil base of the present invention is an oil base containing an ester condensate obtained by a reaction between polyglycerol, 12-hydroxystearic acid, and hydrogenated dimer acid, the oil base having a three-dimensional network structure in which hydrogenated dimer acid is condensed with a hydroxyl group of each of the polyglycerol and 12-hydroxystearic acid.

8 Claims, 4 Drawing Sheets

OIL BASE AND EXTERNAL PREPARATION CONTAINING SAME

CROSS-REFERENCE TO RELATED APPLICATION

This application claims the benefit of U.S. Provisional Application Ser. No. 60/792,286, filed on Apr. 14, 2006, the disclosure of which is incorporated herein by reference.

TECHNICAL FIELD

The present invention relates to an oil base having appropriate hardness and viscosity and excellent spreadability, and an external preparation containing the oil base.

BACKGROUND ART

Conventionally, various ester compounds have been reported as oil bases used for cosmetic materials, etc. For example, JP, A, 2004-256539 (Patent Publication 1) describes a cosmetic composition containing a dispersion having at least one type of liquid fat phase having 1 to 7 carbons and polymer particles dispersed in the fat phase, and at least one type of ester of at least one type of carboxylic acid with a polyhydric alcohol containing at least 4 hydroxyl groups. However, this ester compound is inadequate in terms of properties such as viscosity and spreadability, and is not satisfactory as an oil base used in an external preparation such as a cosmetic material.

As an ester compound used in a cosmetic material, an ester compound obtained by reacting dimer acid and a monohydric or polyhydric alcohol has been examined. For example, JP, A, 2004-256515 (Patent Publication 2) describes an oil base containing an ester in which an oligomer ester of dimer acid with a di- or higher-hydric alcohol is esterified with a monohydric alcohol and/or a monovalent carboxylic acid, or an ester in which an oligomer ester of dimer diol with a di- or higher-valent carboxylic acid is esterified with a monohydric alcohol and/or a monovalent carboxylic acid, and JP, A, 2005-132729 (Patent Publication 3) describes a mixed fatty acid ester obtained by subjecting polyglycerol, dimer acid, and a saturated fatty acid and/or unsaturated fatty acid having 12 to 22 carbons to an esterification reaction. However, these ester compounds are intended to improve gloss, colorant dispersibility, etc. or improve hydration properties, and do not exhibit smooth spreadability, adherence, etc. when applied to skin.

Furthermore, JP, A, 2005-36005 (Patent Publication 4) describes a cosmetic composition containing a cosmetically acceptable medium containing at least one polyester obtained by esterification of an aliphatic hydroxycarboxylic acid ester having at least two hydroxyl groups with a polycarboxylic acid, and at least one hydrocarbon ester other than the polyester. However, this publication gives as a specific example only a polyester of hydrogenated castor oil with dimer dilinoleic acid, and as described in JP, A, 2003-238332 (Patent Publication 5) although such a polyester exhibits effects in terms of an appropriate oily feel, adhesion, emollient properties, etc., it does not give effects in terms of smooth spreadability, a refreshing feel with suppressed stickiness, etc.

On the other hand, JP, A, 2005-179377 (Patent Publication 6) has proposed a hydroxy compound obtained by subjecting diglycerol, isostearic acid, and dimer acid to a condensation reaction. However, although this hydroxy compound exhibits excellent effects in an emulsion, a liquid, etc., the properties required for use in a solid such as appropriate viscosity, slip properties, spreadability, etc. are not sufficient. Furthermore, JP, A, 11-128713 (Patent Publication 7) describes an esterification product of a glycerol polymer, one type or a mixture of two or more types of 12-hydroxystearic acid and/or ricinoleic acid and an intermolecular oligoesterification product of these fatty acids, and an aliphatic saturated dibasic acid having 9 to 20 carbons. However, this esterification product is intended for an emulsion stabilizer, and there is no description of its properties as an external preparation such as a cosmetic material.

[Patent Publication 1] JP, A, 2004-256539
[Patent Publication 2] JP, A, 2004-256515
[Patent Publication 3] JP, A, 2005-132729
[Patent Publication 4] JP, A, 2005-36005
[Patent Publication 5] JP, A, 2003-238332
[Patent Publication 6] JP, A, 2005-179377
[Patent Publication 7] JP, A, 11-128713

DISCLOSURE OF INVENTION

Problems to be Solved by the Invention

Therefore, an object of the present invention is to provide an oil base having appropriate hardness and viscosity and excellent spreadability, and an external preparation containing the oil base.

Means for Solving the Problems

As a result of an intensive investigation taking into account the above-mentioned object, the present inventors have found that an ester condensate obtained by a reaction between polyglycerol, 12-hydroxystearic acid, and hydrogenated dimer acid has a three-dimensional network structure, and consequently has properties such as appropriate hardness, viscosity, and smooth spreadability, and the present invention has thus been accomplished.

That is, the present invention relates to an oil base containing an ester condensate obtained by a reaction between polyglycerol, 12-hydroxystearic acid, and hydrogenated dimer acid, the oil base having a three-dimensional network structure in which hydrogenated dimer acid is condensed with a hydroxyl group of each of polyglycerol and 12-hydroxystearic acid.

Furthermore, the present invention relates to the oil base wherein at least part of the ester-condensed 12-hydroxystearic acid is self-condensed to form a 12-hydroxystearic acid oligomer.

Moreover, the present invention relates to the oil base wherein the polyglycerol is a polyglycerol having an average degree of polymerization of 2 to 4.

Furthermore, the present invention relates to the oil base wherein the ester condensate is obtained by reacting polyglycerol and 12-hydroxystearic acid and reacting an ester compound thus obtained with hydrogenated dimer acid.

Moreover, the present invention relates to the oil base wherein the polyglycerol is diglycerol, and the proportions of diglycerol, 12-hydroxystearic acid, and hydrogenated dimer acid (diglycerol:12-hydroxystearic acid:hydrogenated dimer acid) are 1:1 to 3:0.3 to 0.8 as a molar equivalent ratio.

Furthermore, the present invention relates to an external preparation containing the oil base.

Moreover, the present invention relates to the external preparation wherein it is a cosmetic material.

Furthermore, the present invention relates to the external preparation wherein the cosmetic material is an oily solid cosmetic material.

The ester condensate constituting the oil base of the present invention forms a three-dimensional network structure in which hydrogenated dimer acid is condensed with a hydroxyl group of each of polyglycerol and 12-hydroxystearic acid condensed with polyglycerol, and adjacent ester compounds are thereby crosslinked via the hydrogenated dimer acid. Normally, when a three-dimensional network structure is formed, solidification occurs due to gelling, but surprisingly, in the oil base of the present invention the three-dimensional network structure is formed with good balance by the above-mentioned three components, exhibits solubility or dispersibility in an oil, and has appropriate hardness and viscosity. Although the mechanism of the above-mentioned actions possessed by the oil base of the present invention is not completely clear, it is surmised that, for example, when the oil base of the present invention is made into a cosmetic material, liquid oil is retained within the three-dimensional network structure, when applied to skin there is little crystal cleavage, and the liquid oil retained by the network structure exudes, thus showing smooth spreadability, etc.

Since the oil base of the present invention employs both hydrogenated dimer acid and 12-hydroxystearic acid as carboxylic acids for the ester condensate, control of the reaction is relatively easy, and an ester condensate having a desired hardness and viscosity may be prepared.

Effects of the Invention

The oil base of the present invention contains an ester condensate obtained by a reaction between polyglycerol, 12-hydroxystearic acid, and hydrogenated dimer acid, and has an appropriate three-dimensional network structure. Because of this, it has appropriate hardness, viscosity, spreadability, etc., is not sticky, and is suitable for an external preparation such as a cosmetic material.

BEST MODE FOR CARRYING OUT THE INVENTION

[1] Oil Base

The oil base of the present invention is an oil base containing an ester condensate obtained by a reaction between polyglycerol, 12-hydroxystearic acid, and hydrogenated dimer acid, and has a three-dimensional network structure in which carboxyl groups of hydrogenated dimer acid and a hydroxyl group of each of polyglycerol and 12-hydroxystearic acid are condensed.

In order to form an oil base having a three-dimensional network structure, reacting, for example, polyglycerol and 12-hydroxystearic acid and then reacting the ester compound thus obtained with hydrogenated dimer acid is effective. When polyglycerol and 12-hydroxystearic acid are condensed, the ester compound thus obtained has residual hydroxyl groups of polyglycerol and a hydroxyl group of the esterified 12-hydroxystearic acid (the ester compound preferably has at least three hydroxyl groups). By reacting this ester compound with hydrogenated dimer acid, a crosslinking reaction between adjacent ester compounds via hydrogenated dimer acid occurs to give a three-dimensionally branched star-shaped structure. The branched ester chains are further condensed with each other or are present in the vicinity of each other, thus forming a three-dimensional network structure.

In the present invention, since the carboxyl groups of hydrogenated dimer acid are condensed with hydroxyl groups of both polyglycerol and 12-hydroxystearic acid, a network structure having an appropriate net size is obtained, and when applied to an external preparation, liquid oil, etc. is retained by the three-dimensional network structure, thereby yielding preferred effects such as smooth spreadability and adherence. Furthermore, in the ester condensate, at least some of the 12-hydroxystearic acid is preferably self-condensed to thus form an oligomer. Introducing a structure due to an oligomer of 12-hydroxystearic acid enables an appropriate three-dimensional network structure to be formed, thus yielding more preferable effects as an oil base.

(A) Polyglycerol

The polyglycerol used in the present invention is preferably a polyglycerol having an average degree of polymerization of 2 to 15, more preferably an average degree of polymerization of 2 to 10, and yet more preferably an average degree of polymerization of 2 to 4, and is particularly preferably diglycerol. The polyglycerol may be used singly or as a mixture of two or more types. When the degree of polymerization of the polyglycerol is 1 (i.e. glycerol), 12-hydroxystearic acid and hydrogenated dimer acid, which condense with glycerol, are too close to each other, and it is difficult to form an appropriate three-dimensional network structure. On the other hand, when the degree of polymerization of the polyglycerol is too high, hydrogenated dimer acid preferentially reacts with a hydroxyl group of polyglycerol rather than a hydroxyl group of 12-hydroxystearic acid, and the amount of hydrogenated dimer acid that reacts with a hydroxyl group of 12-hydroxystearic acid is small, thereby making it difficult to form an appropriate three-dimensional network structure.

(B) Hydrogenated Dimer Acid

The dimer acid referred to in the present specification means an aliphatic dibasic acid having a double bond and 36 carbon atoms obtained by dimerization of an unsaturated fatty acid having 18 carbons, and is mainly dimer dioleic acid or dimer dilinoleic acid. Furthermore, the hydrogenated dimer acid referred to here means a saturated aliphatic dibasic acid having 36 carbons formed by reducing the double bond within the above dimer acid, for example, by hydrogenation reduction of the dimer acid. Dimer acid is usually produced using an unsaturated fatty acid having 18 carbons, which is mainly oleic acid or linoleic acid, and is obtained as a mixture containing many compounds including monomer acid, trimer acid, etc. as by-products. The hydrogenated dimer acid used in the present invention may be two or more types of hydrogenated products obtained from the above mixture. Moreover, the hydrogenated dimer acid preferably has the double bond of the dimer acid completely hydrogenated, but the double bond may partially remain. In the present specification, the hydrogenated dimer acid may simply be denoted as dimer dilinoleic acid in accordance with the label name for cosmetics.

The number-average molecular weight of the oil base is preferably 2000 to 10000 g/mol, more preferably 2500 to 6000 g/mol, and yet more preferably 3500 to 4500 g/mol. In the present specification, the number-average molecular weight means a molecular weight obtained by measurement of a relative molecular weight distribution on a polystyrene basis by GPC (gel permeation chromatography). Adjusting the number-average molecular weight so as to be in the above-mentioned range enables an appropriate melting point, lipid solubility, etc. to be obtained, and when made into an external preparation effects such as appropriate hardness and viscosity can be imparted.

The hydroxyl value of the oil base of the present invention is preferably 50 to 300, and more preferably 100 to 200. Adjusting the hydroxyl value so as to be in the above-mentioned range enables an external preparation having high hydration properties and excellent moisture retention and wettability to be obtained. The viscosity (60° C.) is preferably 500 to 12000 (mPa·s), and more preferably 1000 to 5000 (mPa·s). By adjusting the viscosity so as to be in the above-mentioned range, appropriate viscosity is exhibited when applied to an oily solid cosmetic material such as, for example, a lipstick, and excellent sensory properties can be obtained when applied to skin.

In the oil base of the present invention, carboxylic acid in the terminal portion of the ester condensate is preferably esterified. When there is a large amount of free carboxylic acid in the ester condensate, it might cause skin irritation when applied as an external preparation.

The oil base of the present invention is explained in further detail by way of an ester condensate formed from diglycerol, 12-hydroxystearic acid, and hydrogenated dimer acid (hereinafter, also called HSDA), which is one preferred embodiment.

One example of a basic structural unit (oligoesterified material) forming HSDA is shown in comparison with an ester condensate of diglycerol, isostearic acid, and hydrogenated dimer acid (hereinafter, also called ISDA) described in Patent Publication 6 above.

HSDA:

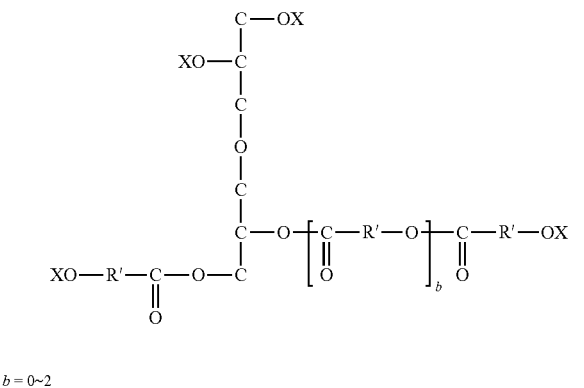

$b = 0\sim 2$

ISDA:

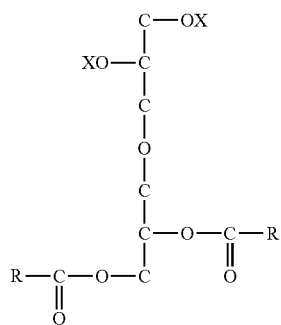

The oligoesterified material of HSDA has at least one 12-hydroxystearic acid (HOR'COOH) condensed with diglycerol (in this example, 12-hydroxystearic acid being condensed with two hydroxyl groups of diglycerol), and hydrogenated dimer acid (X) condensed with a free hydroxyl group of diglycerol that is not esterified by isostearic acid and a hydroxyl group of 12-hydroxystearic acid. 12-Hydroxystearic acid condensed with diglycerol may further be condensed (self-condensed) with 12-hydroxystearic acid. Hydrogenated dimer acid is condensed with a hydroxyl group remaining in diglycerol (preferably two or more remaining hydroxyl groups) and a hydroxyl group of 12-hydroxystearic acid, thus forming a star-shaped branch structure.

On the other hand, with regard to ISDA, isostearic acid (RCOOH) is condensed with diglycerol (in this example, isostearic acid being condensed with two hydroxyl groups of diglycerol), and hydrogenated dimer acid (X) is condensed with a free hydroxyl group of diglycerol that is not esterified by isostearic acid. With regard to ISDA, since there is no hydroxyl group in isostearic acid, isostearic acid does not self-condense. Furthermore, unlike HSDA, hydrogenated dimer acid (X) is not condensed with a hydroxyl group of 12-hydroxystearic acid.

As is clear from the above-mentioned structure, in the case of HSDA, both diglycerol and 12-hydroxystearic acid have free hydroxyl groups, which are condensed with hydrogenated dimer acid to thus form star-shaped branching and further form a three-dimensional network structure via the hydrogenated dimer acid. On the other hand, in the case of ISDA, a reaction with hydrogenated dimer acid results in linear polymerization, and no three-dimensional network structure is formed.

In a structural unit (AB) of HSDA shown in the formula below, a number (degree of bonding) a of 12-hydroxystearic acid (HS) and a self-condensate thereof bound to diglycerol (DG) is preferably 1 to 3. A degree of polymerization b of the self-condensate of 12-hydroxystearic acid is preferably 0 to 2, and it is more preferable for HSDA to at least partially have a self-condensed 12-hydroxystearic acid structure (b=1 to 2). A degree of polymerization n of the oligoesterified materials (AB) themselves is preferably 1 to 3, and a molar equivalent ratio HS:DA of 12-hydroxystearic acid (HS) to hydrogenated dimer acid (DA) is preferably about 1:0.3 to 0.8.

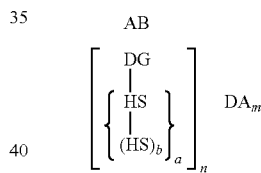

[2] Process for Producing Oil Base

A process for producing the oil base of the present invention may employ any method, but a process involving reacting polyglycerol and 12-hydroxystearic acid and subsequently reacting the ester compound thus obtained with hydrogenated dimer acid is preferable in order to efficiently obtain an ester condensate having an appropriate three-dimensional network structure.

In order to obtain a three-dimensional network structure, it is important for the ester compound obtained by reaction between polyglycerol and 12-hydroxystearic acid to have both a hydroxyl group of polyglycerol and a hydroxyl group of 12-hydroxystearic acid. This allows a star-shaped branched chain to be formed when ester condensation is carried out, thus forming a three-dimensional network structure. When polyglycerol and hydrogenated dimer acid are reacted first and 12-hydroxystearic acid is then reacted therewith, cyclocondensation of polyglycerol and hydrogenated dimer acid proceeds, and hardly any condensation with adjacent esterified material takes place. Furthermore, since the reactivity of hydrogenated dimer acid is high, hydrogenated dimer acid that is added first reacts completely, and the hydroxyl group of 12-hydroxystearic acid that is added later remains rather than condensing with hydrogenated dimer acid. Because of this, the ester compound is not branched in a star shape, and no three-dimensional network structure is formed. Moreover, when polyglycerol, 12-hydroxystearic acid, and hydrogenated dimer acid are reacted at the same time, star-shaped branching can be formed, but since hydrogenated dimer acid and 12-hydroxystearic acid react competitively with polyglycerol, it is not easy to form an appropriate three-dimensional network structure.

In this way, in order to form a three-dimensional network structure not only is the reaction between hydrogenated dimer acid and a hydroxyl group of polyglycerol important, but also the reaction between hydrogenated dimer acid and a hydroxyl group of ester-condensed 12-hydroxystearic acid is important. Reacting hydrogenated dimer acid with both a hydroxyl group of polyglycerol and a hydroxyl group of 12-hydroxystearic acid branching from the polyglycerol enables a three-dimensional network structure exhibiting appropriate hardness and viscosity to be formed easily.

In order to form an appropriate network structure, it is preferable for the molar equivalent ratio of polyglycerol:12-hydroxystearic acid:hydrogenated dimer acid used for ester condensation to be 1:1 to 5:0.3 to 2.5, and more preferably 1:1 to 3:0.3 to 1.5. When diglycerol is used as the polyglycerol, the ratio is preferably 1:1 to 3:0.3 to 0.8, and more preferably 1:1 to 3:0.5 to 0.6. When triglycerol is used as the polyglycerol, the ratio is preferably 1:1 to 4:0.3 to 2.0. Adjusting the ratio of starting materials charged suppresses gelling due to the reaction proceeding too far, and enables an appropriate network structure to be formed.

Reaction conditions for ester condensation are not particularly limited, but in order to obtain a desired three-dimensional network structure, it is desirable that reaction conditions are appropriately selected according to the starting materials, etc. used. The reaction temperature for the ester condensation is preferably 170° C. to 200° C. Examples of a catalyst include sodium hydroxide, p-toluenesulfonic acid, boron trifluoride, hydrogen fluoride, tin chloride, zinc, titanium, potassium hydroxide, a mineral acid (sulfuric acid, hydrochloric acid, etc.), zinc chloride, hypophosphorous acid, and dibutyltin oxide, and it is preferable to use p-toluenesulfonic acid, hypophosphorous acid, etc. The reaction may be carried out without using a catalyst. Examples of a reaction solvent include benzene, toluene, and xylene, and it is preferable to use toluene, xylene, etc. The reaction may be carried out without using a solvent.

One preferred mode for the production process of the present invention involves carrying out a first stage ester condensation reaction between polyglycerol and 12-hydroxystearic acid in the presence of p-toluenesulfonic acid in a nonpolar solvent (benzene, toluene, etc.) at 170° C. to 190° C. while distilling off the water that is produced, and carrying out a second stage ester condensation reaction between the oligoesterified material thus obtained and hydrogenated dimer acid at 180° C. to 200° C. while distilling off the water that is produced. The second stage ester condensation reaction may be carried out subsequent to the first stage ester condensation reaction by adding hydrogenated dimer acid to the reaction mixture as it is, or may be carried out after recovering the esterified material formed in the first stage. The production process of the present invention is not limited to the above-mentioned mode, and it is desirable that the reaction conditions are adjusted appropriately according to the type of polyglycerol starting material, desired physical properties of the oil base, etc.

[3] External Preparation

The external preparation of the present invention is not particularly limited as long as it is an oil base-containing external preparation with application to skin, hair, mucosa, wounds, etc., and includes various types of cosmetic materials, quasi drugs, drugs, etc.

Examples of the cosmetic materials include emulsions, creams (skin cream, lip cream, hair cream, etc.), liquid foundation, eyeliner, mascara, eye shadow gel, lipstick, lip balm, lip gloss, eye gloss, eye color, blusher, body gloss, ointments, soaps, mousses, tonics, and gels.

Examples of the drugs and quasi drugs include lotions, creams, ointments, sprays, aerosols, skin patches, and gels. Examples of active medicinal agents include an anti-infective agent (an antiviral agent, etc.), an analgesic or an analgesic mixture, an arthritis drug, an antidepressant drug, a diabetes drug, an antihistamine agent, an anti-inflammatory agent, a migraine preparation, an antiemetic drug, an antitumor agent, an antipruritic, a psychosis drug, a xanthine derivative, a calcium channel blocker, a beta blocker, an antiarrhythmic agent, an antihypertensive agent, a diuretic, a cardiovascular preparation, a hormone, an immunosuppressive drug, a muscle relaxant, a vasoconstrictor, a vasodilator, a wound healing promoter, an allergy inhibitor, an anti-acne agent, an antiaging agent, an antitussive agent, an antimicrobial agent, a hemorrhoid drug, a local anesthetic, an inflammation inhibitor, and an anticholinergic agent.

The external preparation of the present invention may contain, depending on the intended purpose or as necessary, a skin-whitening agent, a moisturizing agent, an antioxidant, an anti-inflammatory agent, a vitamin, a hormone, an enzyme, a circulation promotion agent, an amino acid, a UV-absorbing agent, a sunscreen agent, a suntan agent, a hair tonic agent (a hair-loss prevention agent, a hair growth promotion agent, etc.), an animal or plant extract, an anti-wrinkle agent, an antiseptic, a hair softener, a hair moisturizer, a makeup preparation, a hair conditioner, a skin conditioner, a hair whitening agent, a chelating agent, a cell replacement promotion agent, a coloring agent, a skin softening agent, a skin moisturizing agent, a deodorant, an antiperspirant, etc.

Examples of the skin-whitening agent include hydroquinone derivatives [hydroquinone glycosides such as α-D-glucose, hydroquinone β-D-glucose (arbutin), hydroquinone α-L-glucose, hydroquinone β-L-glucose, hydroquinone α-D-galactose, hydroquinone β-D-galactose, hydroquinone α-L-galactose, and hydroquinone β-L-galactose, etc.], kojic acid and derivatives thereof, L-ascorbic acid and derivatives thereof [for example, L-ascorbic acid monoesters such as L-ascorbic acid monophosphate and L-ascorbic acid 2-sulfate, L-ascorbic acid glucosides such as L-ascorbic acid 2-glucoside, and salts thereof], tranexamic acid or derivatives thereof [tranexamic acid dimer (trans-4-(trans-aminomethylcyclohexanecarbonyl)aminomethylcyclohexanecarboxylic acid hydrochloride, etc.), esters of tranexamic acid and hydroquinone (4'-hydroxyphenyl trans-4-aminomethylcyclohexanecarboxylate, etc.), esters of tranexamic acid and gentisic acid (2-(trans-4-aminomethylcyclohexylcarbonyloxy)-5-hydroxybenzoic acid and salts thereof, etc.), amides of tranexamic acid (trans-4-aminomethylcyclohexanecarboxylic acid methylamide and salts thereof, etc.)], ellagic acid and derivatives thereof, salicylic acid and derivatives thereof [3-methoxysalicylic acid and salts thereof, 4-methoxysalicylic acid and salts thereof, 5-methoxysalicylic acid and salts thereof, etc.], resorcinol derivatives [alkylresorcinols such as 4-n-butylresorcinol and salts thereof, etc.], and plant extracts having a skin-whitening action.

Examples of the anti-inflammatory agent include glycyrrhizic acid salts (dipotassium glycyrrhizate, ammonium glycyrrhizate, etc.), allantoin, and mixtures thereof.

Examples of antimicrobial agents include resorcin, sulfur, salicylic acid, zinc pyrithione, photosensitizer No. 101, photosensitizer No. 102, Octopirox, hinokitiol, bacitracin, erythromycin, neomycin, tetracycline, chlorotetracycline, benzethonium chloride, phenol, and mixtures thereof.

Examples of the vitamins include vitamins A, C, D, E, and K, vitamin A palmitate, thiamine, vitamin $B_6$, vitamin $B_6$ derivatives such as vitamin $B_6$ hydrochloride, vitamin $B_2$, vitamin $B_{12}$, vitamin B complex such as nicotinic acid, nicotinic acid derivatives such as nicotinamide, pantothenic acid, pantothenyl ethyl ether, pyridoxine, inositol, and carnitine, panthenol, and mixtures thereof.

Examples of the hormone include oxytocin, corticotropin, vasopressin, secretin, gastrin, and calcitonin.

Examples of the enzyme include trypsin, lysozyme chloride, chymotrypsin, chymotrypsin-like enzymes, trypsin, aspartic proteinase, semialkali proteinase, serrapeptase, lipase, and hyaluronidaze.

Examples of the antioxidant include thiotaurine, glutathione, catechin, albumin, ferritin, metallothionein, and the above-mentioned L-ascorbic acid and derivatives thereof.

Examples of blood circulation promoters include acetylcholine derivatives, cepharanthin, and carpronium chloride.

Examples of the amino acids include amphoteric amino acids such as stearyl acetyl glutamate, capryloyl silk amino acid, capryloyl collagen amino acid, capryloyl keratin amino acid, capryloyl p amino acid, cocodimonium hydroxypropyl silk amino acid, corn gluten amino acid, cysteine, glutamic acid, glycine, hair amino acids such as hair keratin amino acid and aspartic acid, threonine, serine, proline, glycine, alanine, half-cystine, valine, methionine, isoleucine, leucine, tyrosine, phenylalanine, cysteic acid, histidine, arginine, cysteine, tryptophan, citrulline, lysine, silk amino acids, wheat amino acids, and mixtures thereof.

Examples of the UV-absorbing agent include benzophenone, bornelone, butyl PABA, cinnamidopropyl trimethyl ammonium chloride, disodium distyrylbiphenyl disulfonate, PABA, potassium methoxycinnamate, and mixtures thereof.

Examples of the sunscreen agent include butylmethoxydibenzoylmethane, octylmethoxycinnamate, octocrylene, octylsalicylate, phenylbenzimidazole sulfonic acid, ethyl hydroxypropylaminobenzoate, menthyl anthranilate, aminobenzoic acid, cinoxate, diethanolamine methoxycinnamate, glyceryl aminobenzoate, titanium dioxide, zinc dioxide, oxybenzone, Padimate-O, red petrolatum, and mixtures thereof.

Examples of the hair tonic agent include blood circulation promoters such as *swertia japonica* extract, acetylcoline derivatives, cepharanthin, and carpronium chloride, local stimulants such as red pepper tincture, *cantharis* extract, and nonylic acid vanillamide, antiseborrhea agents such as pyridoxine and derivatives thereof, antimicrobial agents such as benzalkonium chlorides, isopropylmethylphenol, zinc pyrithione, photosensitizer No. 101, photosensitizer No. 102, Octopirox, and hinokitiol, metabolic stimulants such as photosensitizer No. 301, placenta extract, and biotin, amino acids such as serine, methionine, and tryptophan, and vitamins such as vitamins $B_2$ and $B_{12}$, pantothenic acid, and derivatives thereof.

Among the animal and plant extracts, examples of the plant extract include tea extract, *rosa roxburghii* extract, *scutellaria* root extract, *houttuynia cordata* extract, phellodendri cortex extract, *melilotus officinalis* extract, *lamium album* extract, *glycyrrhiza* extract, paeoniae radix extract, *saponaria officinalis* extract, *luffa cylindrica* extract, *cinchona* extract, saxifrage extract, *sophora angustifolia* extract, *nuphar haponicum* root extract, fennel extract, primrose extract, rose extract, *rehmannia* extract, lemon extract, *lithospermum* root extract, *aloe* extract, iris root extract, *eucalyptus* extract, *equisetum arvense* extract, sage extract, thyme extract, seaweed extract, cucumber extract, clove extract, raspberry extract, *melissa officinalis* extract, carrot extract, horse chestnut extract, peach extract, peach leaf extract, mulberry extract, *centaurea cyanus* extract, witch hazel extract, *glycyrrhiza* extract, *ginkgo* extract, wintergreen extract, *swertia japonica* extract, red pepper tincture extract, and *cantharis* extract. Examples of the animal extract include placenta extract and collagen.

The external preparation of the present invention may contain an oily component other than the oil base of the present invention. As said other oily component, a component of any origin such as an animal oil, a plant oil, a synthetic oil, etc. and a component with any properties such as a solid oil, a semi-solid oil, a liquid oil, a volatile oil, etc. may be used, and examples thereof include hydrocarbons, silicone oils, fats, waxes, hardened oils, ester oils, fatty acids, fatty alcohols, fluorine-containing oils, and lanolin derivatives. Specific examples thereof include hydrocarbons such as light liquid isoparaffin, liquid paraffin, squalane, vaseline, polyisobutylene, and polybutene, oils such as olive oil, castor oil, jojoba oil, mink oil, and *macadamia* nut oil, petroleum waxes such as paraffin wax and microcrystalline wax, mineral waxes such as ozokerite and ceresine, natural waxes such as carnauba wax and candelilla wax, esters such as cetyl isooctanate, isopropyl myristate, isopropyl palmitate, octyldodecyl myristate, glyceryl trioctanoate, polyglyceryl diisostearate, diglyceryl triisostearate, glyceryl tribehenate, pentaerythritol rosinate, neopentyl glycol dioctanoate, and cholesterol fatty acid esters, fatty acids such as stearic acid, lauric acid, myristic acid, behenic acid, isostearic acid, oleic acid, and 12-hydroxystearic acid, fatty alcohols such as stearyl alcohol, cetyl alcohol, lauryl alcohol, oleyl alcohol, isostearyl alcohol, and behenyl alcohol, silicones such as low degree of polymerization dimethylpolysiloxane, decamethylcyclopentasiloxane, octamethylcyclosiloxane, high degree of polymerization dimethylpolysiloxane, methylphenylpolysiloxane, polyether-modified polysiloxane, a polyoxyalkylene/alkylmethylpolysiloxane/methylpolysiloxane copolymer, alkoxy-modified polysiloxane, and fluorine-modified polysiloxane, fluorine-containing oils such as perfluorodecane, perfluorooctane, and perfluoropolyether, and lanolin derivatives such as lanolin, lanolin acetate, lanolin fatty acid isopropyl ester, and lanolin alcohol.

The external preparation of the present invention may contain, in addition to the oil base, the above-mentioned components, etc., as appropriate and as necessary a component that is normally used in an external preparation such as a moisturizing agent, a surfactant, a UV-absorbing agent, a UV-scattering agent, a fragrance, a viscosity increasing agent, an antiseptic, a coloring agent such as an extender pigment or a coloring pigment, or a pH adjusting agent, in a range that does not impair the effects of the present invention.

The form of the external preparation of the present invention is not particularly limited, and it may be in the form of a liquid, an emulsion, a semi-solid agent, a solid agent, etc. according to its intended purpose. The emulsion is not particularly limited and may be any of a water-in-oil type (W/O type) or an oil-in-water type (O/W type), a W/O/W type, and an O/W/O type, etc. For example, in the case of a water-in-oil type emulsion cosmetic material, it is prepared by adding water and a water-soluble component (aqueous phase component) to the oil base. The content ratio of the oil base and the aqueous phase component may be adjusted according to desired properties of the emulsion and is not particularly limited.

The oil base of the present invention is particularly effective when used as a cosmetic material and, in particular, as an oily solid cosmetic material. As a specific example of the oily solid cosmetic material, a lipstick may be produced by, for example, heating and melting the oil base of the present invention as necessary with another oily component, then adding, stirring, and mixing components such as a colorant and an antioxidant, pouring this mixture into a mold, and cooling, thus molding it into a stick shape. Since the oil base of the present invention has high compatibility with other oil bases and excellent spreadability, when applied to the skin as a cosmetic material it spreads smoothly and does not have sticky feel.

EXAMPLES

The present invention is explained in further detail by reference to Examples below, but the present invention should not be construed as being limited thereto.

In these examples, the number-average molecular weight was measured from the relative molecular weight distribution on a polystyrene basis, employing GPC (gel permeation chromatography).
Measurement equipment type: SC-8010 system, manufactured by Tosoh Corporation
Column: 2×Shodex KF-800D+KF-805L
Eluent: THF
Temperature: Thermostated column compartment 40° C.
Flow rate: 1.0 mL/min
Concentration: about 0.2 wt %/vol %
Amount injected: 100/μL
Solubility: Completely dissolved
Detector: Differential refractometer (R1)

The viscosity was measured using a DV-II+Brookfield viscometer (Spindle No. 3, 12 rpm, 60° C.).

The acid value and the hydroxyl value were measured in accordance with General Test Methods 18 Acid Value Measurement Method and 24 Hydroxyl Value Measurement Method, Japanese Standards of Cosmetic Ingredients (new and revised edition, first issue, 30 Aug. 1999).

Example 1

Synthesis of Oil Base 1

A four-necked flask equipped with a stirring device, a thermometer, a Dean-Stark moisture trap, and a nitrogen injection tube was charged with 166 g (1.0 mol) of diglycerol and 452 g (1.5 mol) of 12-hydroxystearic acid, 80 mL of toluene was added as a solvent, p-toluenesulfonic acid was added as a catalyst at 0.05 mass % relative to the total amount charged, and a reaction was carried out at 190° C. to 210° C. for about 6 hours while passing nitrogen gas until the acid value became 2 or less. After the reaction was completed, it was cooled to 80°, 337 g (0.6 mol) of hydrogenated dimer acid was then added thereto, and the reaction was continued again at 200° C. to 210° C. for 5 hours until the acid value became 2 or less (ratio of starting materials charged, that is, diglycerol:12-hydroxystearic acid:hydrogenated dimer acid=1.0:1.5:0.6). Activated clay was added to the reaction mixture thus obtained at 2 mass %, stirring was carried out at 100° C. for 1 hour, the clay was then removed by filtration, and the solvent was removed by blowing in nitrogen under vacuum while heating at 150° C. to give 811 g of an oligomer type oil base of the present invention (oil base 1). This oil base had an acid value of 1.6 and a hydroxyl value of 181. The results are given in Table 1.

Example 2

Synthesis of Oil Base 2

The procedure of Example 1 was repeated except that 133 g (0.8 mol) of diglycerol, 482 g (1.6 mol) of 12-hydroxystearic acid, and 269 g (0.48 mol) of hydrogenated dimer acid (ratio of starting materials charged, that is, diglycerol:12-hydroxystearic acid:hydrogenated dimer acid=1.0:2.0:0.6) were used, and 751 g of an oligomer type oil base was obtained (oil base 2). This oil base had an acid value of 1.6 and a hydroxyl value of 170. The results are given in Table 1.

Example 3

Synthesis of Oil Base 3

The procedure of Example 1 was repeated except that 133 g (0.8 mol) of diglycerol, 542 g (1.8 mol) of 12-hydroxystearic acid, and 269 g (0.48 mol) of hydrogenated dimer acid (ratio of starting materials charged, that is, diglycerol:12-hydroxystearic acid:hydrogenated dimer acid=1.0:2.25:0.6) were used, and 802 g of an oligomer type oil base was obtained (oil base 3). This oil base had an acid value of 1.6 and a hydroxyl value of 155. The results are given in Table 1.

Example 4

Synthesis of Oil Base 4

The procedure of Example 1 was repeated except that 133 g (0.8 mol) of diglycerol, 602 g (2.0 mol) of 12-hydroxystearic acid, and 269 g (0.48 mol) of hydrogenated dimer acid (ratio of starting materials charged, that is, diglycerol:12-hydroxystearic acid:hydrogenated dimer acid=1.0:2.5:0.6) were used, and 853 g of an oligomer type oil base was obtained (oil base 4). This oil base had an acid value of 1.8 and a hydroxyl value of 136. The results are given in Table 1.

Example 5

Synthesis of Oil Base 5

The procedure of Example 1 was repeated except that 133 g (0.8 mol) of diglycerol, 602 g (2.0 mol) of 12-hydroxystearic acid, and 180 g (0.32 mol) of hydrogenated dimer acid (ratio of starting materials charged, that is, diglycerol:12-hydroxystearic acid:hydrogenated dimer acid=1.0:2.0:0.4) were used, and 725 g of an oligomer type oil base was obtained (oil base 5). This oil base had an acid value of 1.3 and a hydroxyl value of 118. The results are given in Table 1.

TABLE 1

|  | Oil base 1 | Oil base 2 | Oil base 3 | Oil base 4 | Oil base 5 |
| --- | --- | --- | --- | --- | --- |
| Molar ratio charged | 1.0:1.5:0.6 | 1.0:2.0:0.6 | 1.0:2.25:0.6 | 1.0:2.5:0.6 | 1.0:2.0:0.4 |
| Yield | 811 | 751 | 802 | 853 | 725 |
| Acid value (AV) | 1.6 | 1.6 | 1.6 | 1.8 | 1.3 |
| Hydroxyl value (OHV) | 181 | 170 | 155 | 136 | 118 |

TABLE 1-continued

|  | Oil base 1 | Oil base 2 | Oil base 3 | Oil base 4 | Oil base 5 |
|---|---|---|---|---|---|
| Number-average molecular weight (Mn) | 3100 | 5900 | 3400 | 3600 | 2100 |
| Viscosity (60° C.) | 2500 | 9050 | 9500 | 9800 | 1010 |

Example 6

Synthesis of Oil Base 6

The same kind of equipment as in Example 1 was charged simultaneously with 133 g (0.8 mol) of diglycerol, 482 g (1.8 mol) of 12-hydroxystearic acid, and 269 g (0.48 mol) of hydrogenated dimer acid (ratio of starting materials charged, that is, diglycerol:12-hydroxystearic acid:hydrogenated dimer acid=1.0:2.0:0.4), 80 ml of toluene was added, p-toluenesulfonic acid was added as a catalyst at 0.05 mass % relative to the total amount charged, and a reaction was continued at 200° C. to 210° C. until the acid value became 2 or less. Activated clay was added to the reaction mixture thus obtained at 2 mass %, stirring was carried out at 100° C. for 1 hour, it was filtered and then heated to 150° C., nitrogen was blown in under vacuum, the solvent was removed, and 728 g of an oligomer type oil base was thus obtained in a one step reaction (oil base 6).

Example 7

Synthesis of Oil Base 7

An oligomer synthesis reaction was carried out by a two step reaction in the same manner as in Example 1 except that 133 g (0.8 mol) of diglycerol, 482 g (2.0 mol) of 12-hydroxystearic acid, and 404 g (0.72 mol) of hydrogenated dimer acid (ratio of starting materials charged, that is, diglycerol:12-hydroxystearic acid:hydrogenated dimer acid=1.0:2.0:0.9) were used, but in this synthetic example the viscosity of the reaction mixture increased during the reaction 2 hours after the hydrogenated dimer acid was added, stirring became difficult, and the reaction was therefore discontinued.

TABLE 2

|  | Oil base 6 | Oil base 7 |
|---|---|---|
| Molar ratio charged | 1.0:2.0:0.4 | 1.0:2.0:0.9 |
| Yield | 728 | Impossible to take out due to solidification |
| Acid value (AV) | 1.9 | Could not be measured |
| Hydroxyl value (OHV) | 122 | Could not be measured |
| Number-average molecular weight (Mn) | 1750 | Could not be measured |
| Viscosity (60° C.) | 400 | Could not be measured |

Example 8

Production of Lip Balm

All the components shown in Table 3 were uniformly dissolved at 95° C. to 100° C. and degassed. The mixture was subsequently poured into an appropriate mold and then cooled to give a lip balm.

TABLE 3

| No. | Component | Content (mass %) |
|---|---|---|
| 1 | Oil base of Example 1 (Oil base 1) | 20 |
| 2 | Isotridecyl isononanoate | 23.9 |
| 3 | Trimethylolpropane triethylhexanoate | 20 |
| 4 | Diisostearyl malate | 15 |
| 5 | Polyglyceryl-2 triisostearate | 6 |
| 6 | Ceresine (mp: 73° C. to 76° C.) | 6 |
| 7 | Polyethylene (mp: 88° C.) | 5 |
| 8 | Microcrystalline wax (mp: 78° C.) | 4 |
| 9 | d-δ-Tocopherol | 0.1 |

Example 9

Production of Lip Balm

All the components shown in Table 4 were uniformly dissolved at 95° C. to 100° C. and degassed. The mixture was subsequently poured into an appropriate mold and then cooled to give a lip balm.

TABLE 4

| No. | Component | Content (mass %) |
|---|---|---|
| 1 | Oil base of Example 4 (Oil base 4) | 20 |
| 2 | Isostearyl neopentanoate | 23 |
| 3 | Pentaerythrityl tetraethylhexanoate | Remainder |
| 4 | Microcrystalline wax (mp: 78° C.) | 4 |
| 5 | Ceresine (mp: 73° C. to 76° C.) | 6 |
| 6 | Polyethylene (mp: 88° C.) | 4.5 |
| 7 | Diisostearyl malate | 15 |
| 8 | Polyglyceryl-2 triisostearate | 6 |
| 9 | d-δ-Tocopherol | 0.1 |

Example 10

Production of Lip Balm

All the components shown in Table 5 were uniformly dissolved at 95° C. to 100° C. and degassed. The mixture was subsequently poured into an appropriate mold and then cooled to give a lip balm.

TABLE 5

| No. | Component | Content (mass %) |
|---|---|---|
| 1 | Oil base of Example 3 (Oil base 3) | 15 |
| 2 | (Polyglyceryl-2 isostearate/dimer dilinoleic acid) copolymer | 5 |
| 3 | Isotridecyl isononanoate | 23 |
| 4 | Trimethylolpropane triethylhexanoate | Remainder |
| 5 | Microcrystalline wax (mp: 78° C.) | 4 |
| 6 | Ceresine (mp: 73° C. to 76° C.) | 6 |
| 7 | Polyethylene (mp: 88° C.) | 5 |
| 8 | Diisostearyl malate | 15 |
| 9 | Polyglyceryl-2 triisostearate | 6 |
| 10 | d-δ-Tocopherol | 0.1 |

Example 11

Production of Lip Balm

All the components shown in Table 6 were uniformly dissolved at 95° C. to 100° C. and degassed. The mixture was subsequently poured into an appropriate mold and then cooled to give a lip balm.

TABLE 6

| No. | Component | Content (mass %) |
| --- | --- | --- |
| 1 | Oil base of Example 2 (Oil base 2) | 15 |
| 2 | Hydrogenated castor oil dimer dilinoleate | 10 |
| 3 | Neopentyl glycol diethylhexanoate | 23 |
| 4 | Triisostearin | Remainder |
| 5 | Jojoba seed oil | 3 |
| 6 | Microcrystalline wax (mp: 78° C.) | 4 |
| 7 | Candelilla wax (mp: 68.5° C. to 72.5° C.) | 5 |
| 8 | Polyethylene (mp: 88° C.) | 5 |
| 9 | Diisostearyl malate | 10 |
| 10 | Polyglyeryl-2 diisostearate | 8 |
| 11 | Purified water | 1 |
| 12 | d-δ-Tocopherol | 0.1 |

Example 12

Production of Lip Balm

All the components shown in Table 7 were uniformly dissolved at 95° C. to 100° C. and degassed. The mixture was subsequently poured into an appropriate mold and then cooled to give a lip balm.

TABLE 7

| No. | Component | Content (mass %) |
| --- | --- | --- |
| 1 | Oil base of Example 4 (Oil base 4) | 17 |
| 2 | Hydrogenated polyisobutene(Note 1) | 8 |
| 3 | Ethylhexyl hydroxystearate | 20 |
| 4 | Glyceryl tri(caprylate/caprate) | Remainder |
| 5 | Squalane | 5 |
| 6 | Microcrystalline wax (mp: 78° C.) | 4 |
| 7 | Ceresine (mp: 73° C. to 76° C.) | 5.5 |
| 8 | Polyethylene (mp: 88° C.) | 5 |
| 9 | Diisostearyl malate | 10 |
| 10 | Polyglyceryl-2 triisostearate | 4 |
| 11 | Polyglyeryl-2 diisostearate | 4 |
| 12 | d-δ-Tocopherol | 0.1 |

Note 1:
Product name Parleam 18 (manufactured by NOF Corporation)

Example 13

Production of Lipstick

Component 8 and components 10 to 12 shown in Table 8 were uniformly dispersed in advance by means of a three-role mill. All of the remaining components and the above dispersion were uniformly dissolved at 95° C. to 100° C. and degassed. The mixture was subsequently poured into an appropriate mold and then cooled to give a lipstick.

TABLE 8

| No. | Component | Content (mass %) |
| --- | --- | --- |
| 1 | Oil base of Example 3 (Oil base 3) | 18 |
| 2 | Jojoba seed oil | 1 |
| 3 | Neopentyl glycol dicaprate | Remainder |
| 4 | Pentaerythrityl tetraisostearate | 19 |
| 5 | Microcrystalline wax (mp: 78° C.) | 5.5 |
| 6 | Candelilla wax (mp: 68.5° C. to 72.5° C.) | 5.8 |
| 7 | Polyethylene (mp: 88° C.) | 5.7 |
| 8 | Diisostearyl malate | 10 |
| 9 | Polyglyceryl-2 triisostearate | 6 |
| 10 | Titanium oxide(Note 2) | 1 |
| 11 | Iron oxide [colcothar] | 1.2 |
| 12 | Red 226 | 0.2 |
| 13 | Titanium oxide, mica [Titanium oxide-coated mica] | 4.8 |
| 14 | d-δ-Tocopherol | 0.1 |

Note 2:
Product name Tipaque CR-30 (manufactured by Ishihara Sangyo Kaisha Ltd.)

Example 14

Production of Lipstick

Component 9 and components 11 to 14 shown in Table 9 were uniformly dispersed in advance by means of a three-role mill. All of the remaining components and the above dispersion were uniformly dissolved at 95° C. to 100° C. and degassed. The mixture was subsequently poured into an appropriate mold and then cooled to give a lipstick.

TABLE 9

| No. | Component | Content (mass %) |
| --- | --- | --- |
| 1 | Oil base of Example 4 (Oil base 4) | 13.7 |
| 2 | (Polyglyceryl-2 isostearate/dimer dilinoleic acid) copolymer | 4.5 |
| 3 | Neopentyl glycol diethylhexanoate | Remainder |
| 4 | Pentaerythrityl tetraisostearate | 15.1 |
| 5 | Phenyl trimethicone(Note 3) | 3 |
| 6 | Microcrystalline wax (mp: 78° C.) | 4.5 |
| 7 | Ceresine (mp: 73° C. to 76° C.) | 5.4 |
| 8 | Polyethylene (mp: 88° C.) | 4.5 |
| 9 | Diisostearyl malate | 12.7 |
| 10 | Polyglyceryl-2 triisostearate | 5.4 |
| 11 | Red 202 | 1.23 |
| 12 | Iron oxide [colcothar] | 0.62 |
| 13 | Blue 1 | 0.43 |
| 14 | Iron oxide [black iron oxide] | 0.22 |
| 15 | Titanium oxide, mica | 1 |
| 16 | Synthetic phlogopite, titanium oxide, iron oxide [glitter agent component] | 4 |
| 17 | d-δ-Tocopherol | 0.1 |

Note 3:
Product name phenyl methicone SH556 (manufactured by Dow Corning Toray)

Example 15

Production of Lip Gloss

All the components shown in Table 10 were uniformly dissolved at 95° C. to 100° C. and degassed. The mixture was subsequently cooled to give a lip gloss.

TABLE 10

| No. | Component | Content (mass %) |
| --- | --- | --- |
| 1 | Oil base of Example 1 (Oil base 1) | 35 |
| 2 | Pentaerythrityl tetraisostearate | Remainder |
| 3 | Octyldodecyl stearoyloxystearate | 10 |
| 4 | Diisostearyl malate | 10 |
| 5 | Polyglyceryl-2 diisostearate | 20 |
| 6 | Dextrin (palmitate/ethylhexanoate) | 4 |
| 7 | Amide terminal polyamide resin | 0.5 |
| 8 | d-δ-Tocopherol | 0.1 |

Example 16

Production of Lip Gloss

All the components shown in Table 11 were uniformly dissolved at 95° C. to 100° C. and degassed. The mixture was subsequently cooled to give a lip gloss.

TABLE 11

| No. | Component | Content (mass %) |
|---|---|---|
| 1 | Oil base of Example 2 (Oil base 2) | 10 |
| 2 | (Polyglyceryl-2 isostearate/dimer dilinoleic acid) copolymer | 30 |
| 3 | Pentaerythrityl tetraisostearate | Remainder |
| 4 | Neopentyl glycol diisononanoate | 8 |
| 5 | Diisostearyl malate | 15 |
| 6 | Polyglyeryl-2 diisostearate | 20 |
| 7 | Polyglyceryl-2 triisostearate | 5 |
| 8 | Dextrin palmitate | 6 |
| 9 | Ester terminal polyamide resin | 1 |
| 10 | d-δ-Tocopherol | 0.1 |

Example 17

Production of Lip Gloss

All the components shown in Table 12 were uniformly solved at 95° C. to 100° C. and degassed. The mixture was subsequently cooled to give a lip gloss.

TABLE 12

| No. | Component | Content (mass %) |
|---|---|---|
| 1 | Oil base of Example 3 (Oil base 3) | 5 |
| 2 | (Polyglyceryl-2 isostearate/dimer dilinoleic acid) copolymer | 20 |
| 3 | Hydrogenated polyisobutene | 20 |
| 4 | Pentaerythrityl tetraisostearate | Remainder |
| 5 | Neopentyl glycol diisostearate | 8 |
| 6 | Squalane | 4 |
| 7 | Diisostearyl malate | 5 |
| 8 | Polyglyeryl-2 diisostearate | 15 |
| 9 | Polyglyceryl-2 triisostearate | 15 |
| 10 | Silylated silica | 1 |
| 11 | Dextrin palmitate | 4.5 |
| 12 | Ester terminal polyamide resin | 0.8 |
| 13 | Carmine | 0.01 |
| 14 | d-δ-Tocopherol | 0.1 |

Example 18

Production of Lip Gloss

All the components shown in Table 13 were uniformly dissolved at 95° C. to 100° C. and degassed. The mixture was subsequently cooled to give a lip gloss.

TABLE 13

| No. | Component | Content (mass %) |
|---|---|---|
| 1 | Oil base of Example 4 (Oil base 4) | 10 |
| 2 | (Polyglyceryl-2 isostearate/dimer dilinoleic acid) copolymer | 30 |
| 3 | Hydrogenated castor oil hydrogenated dimer dilinoleate | 5 |
| 4 | Triethylhexanoin | Remainder |
| 5 | Hexyldecyl isostearate | 8 |
| 6 | Jojoba seed oil | 1 |
| 7 | Diisostearyl malate | 12 |
| 8 | Polyglyeryl-2 diisostearate | 20 |
| 9 | Microcrystalline wax | 1 |
| 10 | Dextrin (palmitate/ethylhexanoate) | 4 |
| 11 | Amide terminal polyamide resin | 0.6 |
| 12 | d-δ-Tocopherol | 0.1 |

Example 19

Production of Lip Gloss

Component 5 and components 9 to 11 shown in Table 14 were uniformly dispersed in advance by means of a three-role mill. All of the remaining components and the above dispersion were uniformly dissolved at 95° C. to 100° C. and degassed. The mixture was subsequently poured into an appropriate mold and then cooled to give a lip gloss.

TABLE 14

| No. | Component | Content (mass %) |
|---|---|---|
| 1 | Oil base of Example 4 (Oil base 4) | 20 |
| 2 | Jojoba seed oil | 1 |
| 3 | Neopentyl glycol dicaprate | 9 |
| 4 | Pentaerythrityl tetraisostearate | Remainder |
| 5 | Diisostearyl malate | 10 |
| 6 | Polyglyceryl-2 triisostearate | 20 |
| 7 | Dextrin (palmitate/ethylhexanoate) | 3 |
| 8 | Beeswax | 1 |
| 9 | Titanium oxide(Note 4) | 1 |
| 10 | Iron oxide [colcothar] | 1.2 |
| 11 | Red 226 | 0.2 |
| 12 | Titanium oxide, mica [Titanium oxide-coated mica] | 0.5 |
| 13 | d-δ-Tocopherol | 0.1 |

Note 4: Product name Tipaque CR-30 (manufactured by Ishihara Sangyo Kaisha Ltd.)

Example 20

Production of Lip Gloss

Component 6 and components 11 to 14 shown in Table 15 were uniformly dispersed in advance by means of a three-role mill. All of the remaining components and the above dispersion were uniformly dissolved at 95° C. to 100° C. and degassed. The mixture was subsequently poured into an appropriate mold and then cooled to give a lip gloss.

TABLE 15

| No. | Component | Content (mass %) |
|---|---|---|
| 1 | Oil base of Example 2(Oil base 2) | 20 |
| 2 | (Polyglyceryl-2 isostearate/dimer dilinoleic acid) copolymer | 5 |
| 3 | Neopentyl glycol diethylhexanoate | 15 |
| 4 | Pentaerythrityl tetraisostearate | Remainder |
| 5 | Phenyl trimethicone(Note 5) | 2 |
| 6 | Diisostearyl malate | 5 |
| 7 | Polyglyceryl-2 triisostearate | 20 |
| 8 | Amide terminal polyamide resin | 3 |
| 9 | Dimethylsilylated silica | 1 |
| 10 | Microcrystalline wax | 1 |
| 11 | Red 202 | 1.23 |
| 12 | Iron oxide [colcothar] | 0.62 |
| 13 | Blue 1 | 0.43 |
| 14 | Iron oxide [black iron oxide] | 0.22 |
| 15 | Titanium oxide, mica | 1 |
| 16 | Synthetic phlogopite, titanium oxide, iron oxide [glitter agent component] | 0.6 |
| 17 | d-δ-Tocopherol | 0.1 |

Note 5: Product name phenyl methicone SH556 (manufactured by Dow Corning Toray)

Example 21

Production of Skin Cream (O/W Type Cream)

Composition A and composition B shown in Table 16 were individually dissolved uniformly at 75° C. to 80° C. Composition B was added to composition A while stirring, and emulsified by means of a homo-mixer. The mixture was subsequently cooled to 30° C. while stirring, thus giving a skin cream.

TABLE 16

| | No. | Component | Content (mass %) |
|---|---|---|---|
| A | 1 | Neopentyl glycol diethylhexanoate | 8 |
| | 2 | Squalane | 7 |
| | 3 | Oil base of Example 3 (Oil base 3) | 1 |
| | 4 | (Polyglyceryl-2 isostearate/dimer dilinoleic acid) copolymer | 2 |
| | 5 | Polyglyceryl-10 isostearate | 1.5 |
| | 6 | Behenyl alcohol | 1.5 |
| | 7 | Stearyl stearate | 3 |
| | 8 | Diglyerol, 12-hydroxylstearate ester | 3 |
| | 9 | Pentyl glycol | 3 |
| B | 10 | Glycerol | 5 |
| | 11 | Na stearoyl glutamate | 0.4 |
| | 12 | Xanthan gum | 0.2 |
| | 13 | Carbomer | 0.2 |
| | 14 | Purified water | Remainder |
| | 15 | K hydroxide | 0.05 |

Example 22

Production of Emollient Cream (W/O Type Cream)

Composition A, composition B, and composition C shown in Table 17 were individually dissolved uniformly at 75° C. to 80° C. Composition B was added to composition A while stirring, composition C was gradually added to the mixture thus obtained (gel phase), and it was then emulsified by means of a homo-mixer. The mixture was subsequently cooled to 30° C. while stirring, thus giving an emollient cream.

TABLE 17

| | No. | Component | Content(mass %) |
|---|---|---|---|
| A | 1 | Polyglyceryl-2 isostearate | 1.2 |
| | 2 | Polyglyceryl-3 diisostearate | 2.4 |
| | 3 | Polyglyceryl-10 isostearate | 1.6 |
| | 4 | Squalane | 8 |
| | 5 | Neopentyl glycol diethylhexanoate | 7 |
| | 6 | Oil base of Example 4 (Oil base 4) | 1 |
| | 7 | Dextrin(palmitate/ethylhexanoate) | 0.5 |
| | 8 | Microcrystalline wax | 4 |
| B | 16 | Glycerol | 8 |
| | 17 | Purified water | 3 |
| C | 18 | Pentylene glycol | 3 |
| | 19 | Purified water | Remainder |

Example 23

Productuion of Emulsion Type Foundation (W/O Type Foundation)

Components 9 to 13 shown in Table 18 were dispersed in advance in components 5 and 6 by means of a homo-mixer. Composition A, composition B, and composition C were individually dissolved uniformly at 75° C. to 80° C. subsequently, composition B was gradually added to composition A while stirring, composition C was added to the mixture of composition A and composition B and then emulsfied by means of a homo-mixer. The mixture was subsequently cooled to 30° C. while stirring, thus giving an emulsion type foundation.

TABLE 18

| | No. | Component | Content (mass %) |
|---|---|---|---|
| A | 1 | Polyglyceryl-2 isostearate | 1.2 |
| | 2 | Polyglyceryl-3 diisostearate | 2.5 |
| | 3 | Polyglyceryl-10 isostearate | 1.2 |
| | 4 | Polyglyceryl-10 laurate | 0.3 |
| | 5 | Squalane | 8 |
| | 6 | Hexyldecyl ethylhexanoate | 8 |
| | 7 | Oil base of Example 1(Oil base 1) | 1.5 |
| | 8 | Dextrin(palmitate/ethylhexanoate) | 0.5 |
| | 9 | Talc | 6 |
| | 10 | Titanium oxide | 10 |
| | 11 | Iron oxide [red iron oxide] | 0.05 |
| | 12 | Iron oxide [blue iron oxide] | 0.5 |
| | 13 | Iron oxide [black iron oxide] | 0.03 |
| | 14 | Microcrystalline wax | 1 |
| | 15 | UV inhibitor | As appropriate |
| B | 16 | Glycerol | 10 |
| | 17 | Purified water | 4 |
| C | 18 | Pentylene glycol | 3 |
| | 19 | Purified water | Remainder |

Example 24

Production of Hair Wax

Composition A and composition B shown in Table 19 were individually dissolved uniformly at 75° C. to 80° C. Composition A was added to composition B while stirring and emulsified by means of a homo-mixer. The mixture was subsequently cooled to 30° C. while stirring, thus giving a hair wax.

TABLE 19

| | No. | Component | Content (mass %) |
|---|---|---|---|
| A | 1 | Oil base of Example 2 (Oil base 2) | 2 |
| | 2 | Neopentyl glycol diethylhexanoate | 5 |
| | 3 | Ceresine (mp: 68° C. to 75° C.) | 2.5 |
| | 4 | Candelilla wax (mp: 68.5° C. to 72.5° C.) | 7.5 |
| | 5 | (Polyglyceryl-2 isostearate/dimer dilinoleic acid) copolymer | 4.5 |
| | 6 | Polyglyceryl-10 isostearate | 1.5 |
| | 7 | Dimethicone | 2 |
| | 8 | Behenyl alcohol | 2.5 |
| | 9 | Glyceryl stearate | 2 |
| | 10 | Pentyl glycol | 3 |
| | 11 | Dodecylhexadecanol | 2 |
| B | 12 | Na stearoyl glutamate | 0.6 |
| | 13 | Hydroxypropylmethylcellulose | 0.6 |
| | 14 | Purified water | Remainder |

Example 25

Production of Eye Gloss

Components 4 and 8 shown in Table 20 were uniformly dispersed in advance by means of a three-roll mill. All the remaining components and the above dispersion were dissolved uniformly at 95° C. to 100° C. and degassed. The mixture was subsequently cooled to give an eye gloss.

TABLE 20

| No. | Component | Content (mass %) |
|---|---|---|
| 1 | Oil base of Example 3 (Oil base 3) | 20 |
| 2 | (Polyglyceryl-2 isostearate/dimer dilinoleic acid) copolymer | 2 |
| 3 | Hexyldecyl ethylhexanoate | Remainder |
| 4 | Diisostearyl malate | 3 |

TABLE 20-continued

| No. | Component | Content (mass %) |
|---|---|---|
| 5 | Polyglyeryl-2 diisostearate | 30 |
| 6 | Amide terminal polyamide resin | 8 |
| 7 | Silylated silica | 1 |
| 8 | Blue 1 | 0.43 |
| 9 | (PET/polymethyl methacrylate) laminate [glitter agent component] | 0.5 |
| 10 | UV inhibitor | As appropriate |
| 11 | d-δ-Tocopherol | 0.1 |

Comparative Example 1

Production of Lip Balm

A lip balm was prepared in the same manner as in Example 8 except that an oligomer described in Patent Publication 5 was used instead of the oil base described in Example 1.

TABLE 21

| No. | Component | Content (mass %) |
|---|---|---|
| 1 | Oligomer described in Patent Publication 5 (hydrogenated castor oil dimer dilinoleate) | 20 |
| 2 | Isotridecyl isononanoate | 23.9 |
| 3 | Trimethylolpropane triethylhexanoate | 20 |
| 4 | Diisostearyl malate | 15 |
| 5 | Polyglyceryl-2 triisostearate | 6 |
| 6 | Ceresine (mp: 73° C. to 76° C.) | 6 |
| 7 | Polyethylene (mp: 88° C.) | 5 |
| 8 | Microcrystalline wax (mp: 78° C.) | 4 |
| 9 | d-δ-Tocopherol | 0.1 |

Comparative Example 2

Production of Lip Balm

A lip balm was prepared in the same manner as in Example 8 except that a hydroxy compound described in Patent Publication 6 was used instead of the oil base described in Example 1.

TABLE 22

| No. | Component | Content (mass %) |
|---|---|---|
| 1 | Hydroxy compound described in Patent Publication 6 (Polyglyceryl-2 isostearate/dimer dilinoleic acid) copolymer | 20 |
| 2 | Isotridecyl isononanoate | 23.9 |
| 3 | Trimethylolpropane triethylhexanoate | 20 |
| 4 | Diisostearyl malate | 15 |
| 5 | Polyglyceryl-2 triisostearate | 6 |
| 6 | Ceresine (mp: 73° C. to 76° C.) | 6 |
| 7 | Polyethylene (mp: 88° C.) | 5 |
| 8 | Microcrystalline wax (mp: 78° C.) | 4 |
| 9 | d-δ-Tocopherol | 0.1 |

Comparative Example 3

Production of Lip Balm

A lip balm was prepared in the same manner as in Example 8 except that an esterification product described in Synthetic Example 1 of Patent Publication 7 was used instead of the oil base described in Example 1.

TABLE 23

| No. | Component | Content (mass %) |
|---|---|---|
| 1 | Esterification product described in Synthetic Example 1 of Patent Publication 7 (decaglycerol, 12-hydroxystearic acid, eicosanic diacid ester) | 20 |
| 2 | Isotridecyl isononanoate | 23.9 |
| 3 | Trimethylolpropane triethylhexanoate | 20 |
| 4 | Diisostearyl malate | 15 |
| 5 | Polyglyceryl-2 triisostearate | 6 |
| 6 | Ceresine (mp: 73° C. to 76° C.) | 6 |
| 7 | Polyethylene (mp: 88° C.) | 5 |
| 8 | Microcrystalline wax (mp: 78° C.) | 4 |
| 9 | d-δ-Tocopherol | 0.1 |

(Test of Properties)

The lip balms of Example 8 and Comparative Examples 1 to 3 were subjected to tests of their properties with respect to the items below. The results of each test were evaluated using A: very good, B: good, C: somewhat poor, and D: poor. All of the lip balms used were loaded into wind-out containers.

(1) Hardness

Measurement was carried out using an EZ-Test-20N hardness meter (manufactured by Shimadzu Corporation). Values for stress under conditions of a needle diameter of 1.0 mmΦ, a test speed of 10 mm/min, a temperature of 25° C., and a penetration depth of 10 mm were measured. The average value was defined as the hardness (N).

TABLE 24

(Hardness measurement test results)

| | Example 8 | Comparative Example 1 | Comparative Example 2 | Comparative Example 3 |
|---|---|---|---|---|
| Hardness (N) | 0.30 | 0.23 | 0.33 | 0.48 |
| Evaluation | A | C | A | C |

Evaluation criteria A: at least 0.3 but no more than 0.4, B: at least 0.25 but less than 0.3, or more than 0.4 but no more than 0.45, C: at least 0.2 but less than 0.25, or more than 0.45 but no more than 0.5, D: other than above (2) Shape Retention Properties An evaluation was carried out by measuring the hardness of a lip balm stored at low temperature (5° C.), normal temperature (25° C.), and high temperature (35° C.). Measurement of hardness (shape retention property-1) was carried out under the same conditions as in (1) above. It can be said that shape retention property-1 is excellent when the hardness at each temperature is in a predetermined range and variation in hardness from low temperature through normal temperature to high temperature is small. A change ratio (shape retention property-2) was compared using values for change ratio calculated by the equations below.

Change ratio-1=hardness at 5° C./hardness at 25° C.

Change ratio-2=hardness at 25° C./hardness at 50° C.

TABLE 25

(Shape retention property-1 test results)
Hardness at each temperature

| | Example 8 | Comparative Example 1 | Comparative Example 2 | Comparative Example 3 |
|---|---|---|---|---|
| Hardness at 5° C. (N) | 0.50 (A) | 0.38 (A) | 0.60 (B) | 0.85 (D) |
| Hardness at 25° C. (N) | 0.30 (A) | 0.23 (B) | 0.33 (A) | 0.48 (B) |

TABLE 25-continued (Shape retention property-1 test results)
Hardness at each temperature

|  | Example 8 | Comparative Example 1 | Comparative Example 2 | Comparative Example 3 |
|---|---|---|---|---|
| Hardness at 35° C. (N) | 0.15 (A) | 0.15 (A) | 0.14 (B) | 0.18 (A) |

Evaluation criteria:
Hardness at 5° C. A: at least 0.3 but no more than 0.5, B: more than 0.5 but no more than 0.7, C: more than 0.7 but no more than 0.8, D: other than above
Hardness at 25° C. A: at least 0.3 but no more than 0.4, B: more than 0.2 but less than 0.3, or more than 0.4 but no more than 0.5, C: at least 0.15 but less than 0.2, or more than 0.5 but no more than 0.55, D: other than above
Hardness at 35° C. A: at least 0.15 but no more than 0.20, B: at least 0.10 but less than 0.15, or more than 0.2 but no more than 0.25, C: at least 0.05 but less than 0.10, D: other than above

TABLE 26

(Shape retention property-2 test results)
Rate of change

|  | Example 8 | Comparative Example 1 | Comparative Example 2 | Comparative Example 3 |
|---|---|---|---|---|
| Change ratio-1 | 1.7 (A) | 1.7 (A) | 1.8 (A) | 1.8 (A) |
| Change ratio-2 | 2.0 (B) | 1.5 (A) | 2.4 (B) | 2.7 (D) |

Evaluation criteria:
Change ratio A: at least 1.0 but no more than 2.0, B: at least 2.0 but no more than 2.4, C: more than 2.4 but no more than 2.6, D: more than 2.6 but no more than 3.0

(3) Break Strength

Measurement was carried out using an EZ-Test-20N hardness meter (manufactured by Shimadzu Corporation). A container was fixed horizontally, a jig for applying a load was abutted against a side face of a wound-out stick at a position 10 mm from the end of a receiving plate for the stick, and a load was applied at a speed of 50 mm/min. Measurements for stress (N) and breaking point (break position (mm) when needle penetrated) when broken were defined as a break strength (N) and a breaking point (mm).

TABLE 27

(Break strength measurement test results)

|  | Example 8 | Comparative Example 1 | Comparative Example 2 | Comparative Example 3 |
|---|---|---|---|---|
| Break strength (N) | 3.2 | 2.2 | 3.1 | 2.7 |
| Breaking point (mm) | 3.0 | 3.0 | 3.5 | 2.0 |
| Overall evaluation | A | B | A | C |

Evaluation criteria:
Break strength A: at least 3.0 but no more than 4.0, B: at least 2.0 but less than 3, or more than 4.0 but no more than 4.5, C: at least 1.5 but less than 2.0, D: other than above
Breaking point A: at least 3.0 but no more than 4.0, B: at least 2.5 but less than 3, C: more than 4.0 but no more than 4.5, D: other than above (4) Slip Properties Measurement was carried out using a frictional feel tester (manufactured by Kato Tech Co., Ltd.), a lipstick fixing jig, and an artificial leather (manufactured by Idemitsu Petrochemical Co., Ltd.). A stick was wound out from a lipstick container, a middle part thereof was sectioned, and a middle part thereof was sectioned to give a sample. The lipstick container was fixed by means of the fixing jig so as to face vertically downward, the sectioned face (diameter 12.5 mm) was applied in a double pass to the same position on the surface of the artificial leather at 35° C. and a speed of 1 mm/sec, and an average coefficient of friction (MIU) was measured. The double pass movement was repeated three times, and an average value was used to evaluate the slip properties. The sample stage and the artificial leather were maintained at 35° C.

TABLE 28

(Slip properties test results)

|  | Example 8 | Comparative Example 1 | Comparative Example 2 | Comparative Example 3 |
|---|---|---|---|---|
| Slip properties (1 double pass) | 2.32 (A) | 2.05 (A) | 2.83 (C) | 2.48 (B) |
| Slip properties (2 double passes) | 1.42 (A) | 1.32 (A) | 1.90 (C) | 1.79 (B) |
| Slip properties (3 double passes) | 1.31 (A) | 1.28 (A) | 1.82 (D) | 1.65 (B) |
| Average value for 3 double passes | 1.68 (A) | 1.55 (A) | 2.18 (D) | 1.97 (C) |
| Evaluation (slip properties for 3 double passes) | A | A | D | C |

* A difference of 0.5 or more can be recognized by the human senses.
Evaluation criteria:
First double pass A: at least 2.0 but no more than 2.4, B: more than 2.4 but no more than 2.6, C: more than 2.6 but no more than 3.0, D: >3.0
Second double pass A: at least 1.2 but no more than 1.5, B: more than 1.5 but no more than 1.8, C: more than 1.8 but no more than 2.0, D: >2.0
Third double pass A: at least 1.2 but no more than 1.5, B: more than 1.5 but no more than 1.7, C: more than 1.7 but no more than 1.8, D: >1.8
Average A: at least 1.4 but no more than 1.8, B: more than 1.8 but no more than 1.9, C: more than 1.9 but no more than 2.0, D: >2.0

(5) Adherence

Measurement was carried out using a frictional feel tester (manufactured by Kato Tech Co., Ltd.), a lipstick fixing jig, an artificial leather (manufactured by Idemitsu Petrochemical Co., Ltd.), and an XS205DU analytical balance (Metler-Toledo K.K.). A stick was wound out from a lipstick container, and a middle part thereof was sectioned to give a sample. The lipstick container was fixed by means of the fixing jig so as to face vertically downward, the sectioned face (diameter 12.5 mm) was applied in a double pass to the same position on the surface of the artificial leather at 35° C. and a speed of 1 mm/sec, and an amount adhering (mg) was measured. The double pass movement was repeated three times, and the average of the values was used to evaluate the adherence. The sample stage and the artificial leather were maintained at 35° C.

TABLE 29

(Adherence test results)

|  | Example 8 | Comparative Example 1 | Comparative Example 2 | Comparative Example 3 |
|---|---|---|---|---|
| Adherence (1 double pass) | 6.07 (A) | 4.90 (C) | 7.70 (A) | 3.92 (D) |
| Adherence (2 double passes) | 8.81 (A) | 7.23 (B) | 10.80 (A) | 5.77 (D) |
| Adherence (3 double passes) | 11.19 (A) | 9.92 (C) | 12.20 (A) | 7.80 (D) |
| Evaluation (adherence for 3 double passes) | A | C | A | D |

Evaluation criteria:
First double pass A: at least 6.0, B: at least 5.0 but less than 6.0, C: at least 4.0 but less than 5.0, D: less than 4.0
Second double pass A: at least 8.0, B: at least 7.0 but less than 8.0, C: at least 6.0 but less than 7.0, D: less than 6.0
Third double pass A: at least 11.0, B: at least 10.0 but less than 11.0, C: at least 9.0 but less than 10.0, D: less than 9.0

(6) Crystalline State

The crystalline state was evaluated by observation using a BX-51 optical microscope (manufactured by Olympus Corporation) at a magnification of 1000, as well as by visual observation of appearance. The evaluation criteria were as shown below. The crystalline state affects sweating (oil droplets exuding onto the surface of a stick) and the feel when used.

TABLE 30

| Evaluation score | Evaluation criteria | Size of crystals (μm) |
|---|---|---|
| A | Fine and uniform crystals | <11 |
| B | Medium size crystals | At least 12 but no more than 15 |
| C | Somewhat large and non-uniform crystals | At least 11 but less than 12 and/or more than 15 but no more than 16 |
| D | Large and non-uniform crystals | >16 |

TABLE 31

Results of observation of crystalline state

| | Example 8 | Comparative Example 1 | Comparative Example 2 | Comparative Example 3 |
|---|---|---|---|---|
| Crystalline state | See FIG. 1 | See FIG. 2 | See FIG. 3 | See FIG. 4 |
| Evaluation results | A Fine and uniform crystals | A Fine and uniform crystals | D Large and non-uniform crystals | C Somewhat large and non-uniform crystals |

Evaluation results for Example 8 and Comparative Examples 1 to 3 are summarized below.

TABLE 32

| | Example 8 | Comparative Example 1 | Comparative Example 2 | Comparative Example 3 |
|---|---|---|---|---|
| Hardness | A | C | A | B |
| Shape retention properties | A | A | B | C |
| Break strength | A | B | A | C |
| Slip properties | A | A | D | C |
| Adherence | A | C | A | D |
| Crystalline state | A | A | D | C |
| Overall evaluation | A | B | C | D |

Evaluation criteria:
A: Very good,
B: Good,
C: Somewhat poor,
D: Poor

It has been found from the test results of (1) to (6) above that the performance of a cosmetic material depends greatly on the properties of the oil base. In Example 8, in which the oil base of the present invention was used, very satisfactory results were obtained with respect to all of the items required for a lip balm (hardness, break strength, slip properties, adherence, crystalline state). On the other hand, Comparative Example 1, in which an oligomer described in Patent Publication 5 was used, exhibited somewhat poor hardness and adherence, and Comparative Example 2, in which a hydroxy compound described in Patent Publication 6 was used, exhibited poor results in terms of slip properties and crystalline state. The oil bases described in Comparative Examples 1 and 2 are different from the oil base of the present invention not only with respect to the constitutional components, but also in that they do not have a three-dimensional network structure, and it is surmised that this affects the performance. Furthermore, it has been found that an esterification product described in Comparative Example 3 is for stabilizing an emulsion, is different from the oil base of the present invention with respect to the constitutional components and the structure, and does not satisfy the performance requirements for a cosmetic material such as a lip balm.

Figure 1:
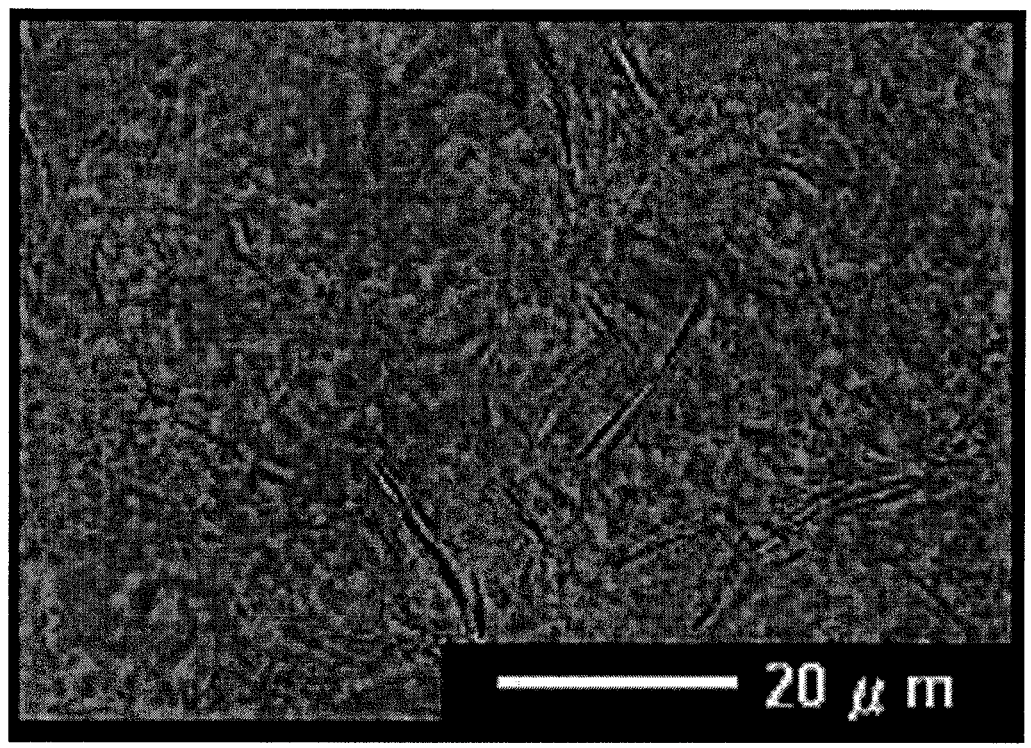
FIG. 1 A photomicrograph showing the crystalline state of the lip balm described in Example 8.
Figure 2:
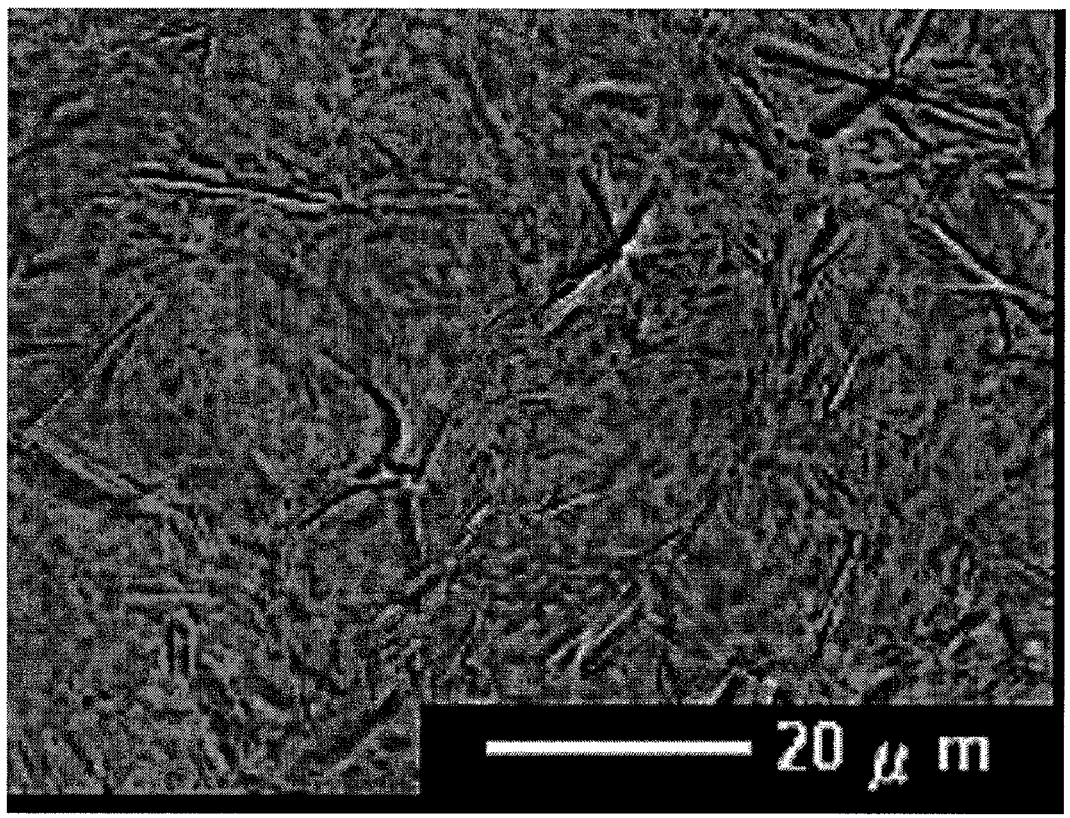
FIG. 2 A photomicrograph showing the crystalline state of the lip balm described in Comparative Example 1.
Figure 3:
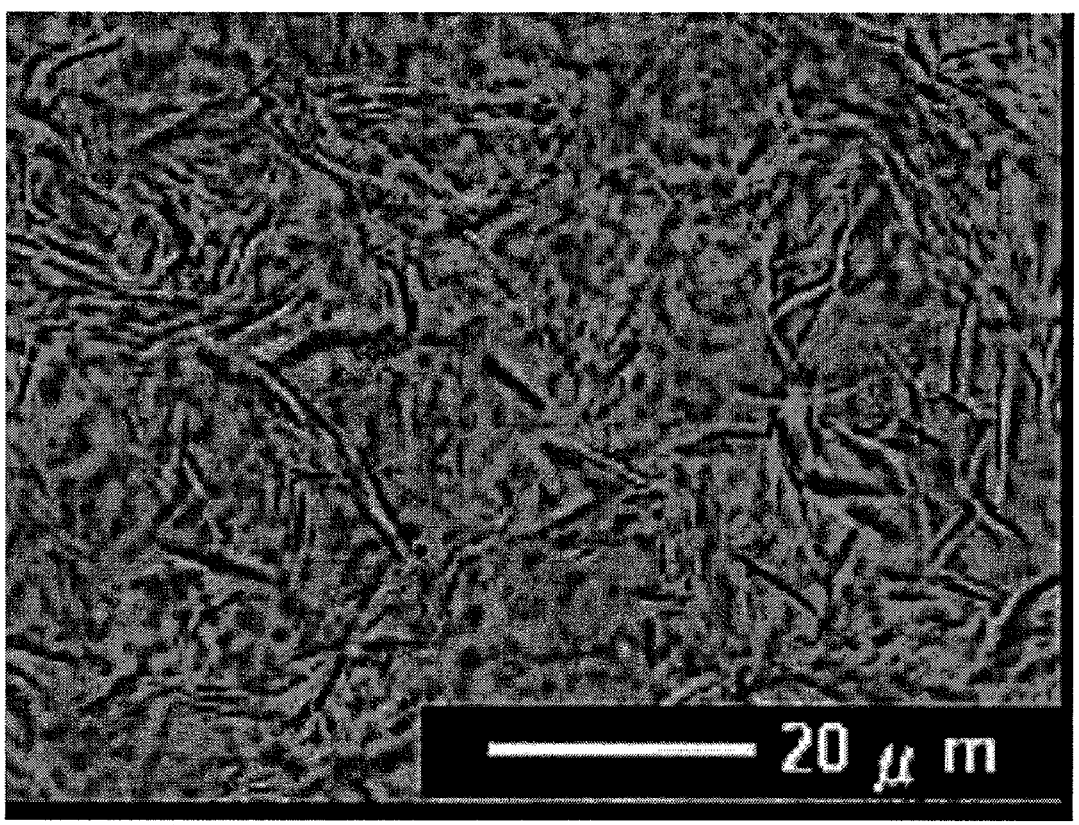
FIG. 3 A photomicrograph showing the crystalline state of the lip balm described in Comparative Example 2.
Figure 4:
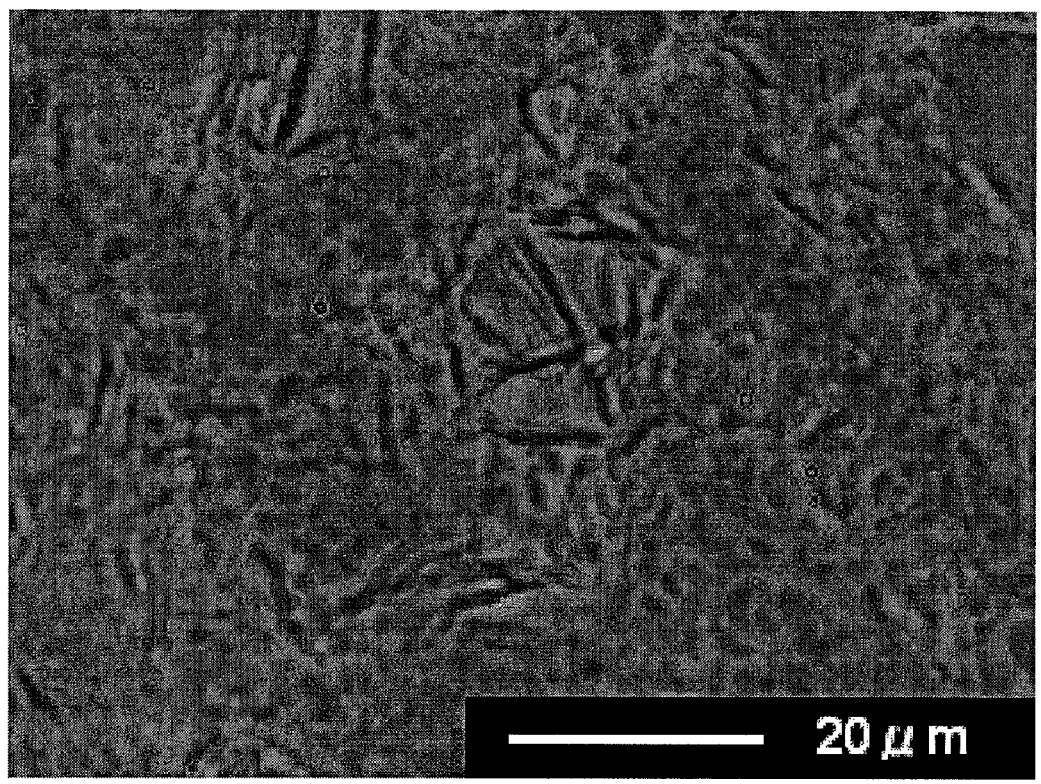
FIG. 4 A photomicrograph showing the crystalline state of the lip balm described in Comparative Example 3.

The invention claimed is:

1. An oil base containing an ester condensate obtained by reacting polyglycerol and 12-hydroxystearic acid to form an ester compound having both a hydroxyl group of polyglycerol and a hydroxyl group of 12-hydroxystearic acid, and
reacting the ester compound thus obtained with hydrogenated dimer acid to form the ester condensate, having a three-dimensional network structure in which hydrogenated dimer acid is condensed with a hydroxyl group of each of polyglycerol and 12-hydroxystearic acid,
wherein the hydrogenated dimer acid is a saturated aliphatic dibasic acid having 36 carbons.

2. The oil base according to claim 1, wherein at least part of the ester-condensed 12-hydroxystearic acid is self-condensed to form a 12-hydroxystearic acid oligomer.

3. The oil base according to claim 1, wherein the polyglycerol is a polyglycerol having an average degree of polymerization of 2 to 4.

4. The oil base according to claim 1, wherein the polyglycerol is diglycerol, and the proportions of diglycerol, 12-hydroxystearic acid, and hydrogenated dimer acid (diglycerol:12-hydroxystearic acid:hydrogenated dimer acid) are 1:1 to 3:0.3 to 0.8 as a molar equivalent ratio.

5. An external preparation containing the oil base according to any one of claims 1 to 3 and 4.

6. The external preparation according to claim 5, wherein it is a cosmetic material.

7. The external preparation according to claim 6, wherein the cosmetic material is an oily solid cosmetic material.

8. A method for producing an oil base containing an ester condensate having a three-dimensional network structure in which hydrogenated dimer acid is condensed with a hydroxyl group of each of polyglycerol and 12-hydroxystearic acid, wherein the hydrogenated dimer acid is a saturated aliphatic dibasic acid having 36 carbons, comprising following steps:
reacting polyglycerol and 12-hydroxystearic acid, and
reacting an ester compound thus obtained with hydrogenated dimer acid.

* * * * *